United States Patent [19]

Dixon, Jr.

[11] Patent Number: 4,782,501
[45] Date of Patent: Nov. 1, 1988

[54] METHOD FOR DETERMINING PORE VOLUME COMPRESSIBILITY OF A POROUS MATERIAL

[75] Inventor: James R. Dixon, Jr., Dallas, Tex.

[73] Assignee: Mobil Oil Corporation, New York, N.Y.

[21] Appl. No.: 93,278

[22] Filed: Sep. 4, 1987

[51] Int. Cl.$^4$ ............................................. G01N 23/06
[52] U.S. Cl. .......................................... 378/4; 378/51; 250/253; 250/255
[58] Field of Search ................... 378/4, 51, 54, 55, 56; 250/253, 255

[56] References Cited

U.S. PATENT DOCUMENTS

| | | | |
|---|---|---|---|
| 3,839,899 | 10/1974 | McMillen | 73/38 |
| 4,157,472 | 6/1979 | Beck, Jr. et al. | 250/443 |
| 4,283,629 | 8/1981 | Habermehl et al. | 250/445 |
| 4,399,509 | 8/1983 | Hounsfield | 364/414 |
| 4,422,177 | 12/1983 | Mastronardi et al. | 378/17 |
| 4,618,975 | 10/1986 | Glantschnig | 378/51 |
| 4,649,483 | 3/1987 | Dixon, Jr. | 364/422 |
| 4,671,102 | 6/1987 | Vinegar et al. | 378/52 |
| 4,688,238 | 8/1987 | Sprunt et al. | 378/4 |
| 4,722,095 | 1/1988 | Muegge et al. | 378/51 |

OTHER PUBLICATIONS

"Petroleum Production Engineering", L. C. Uren, 4th Ed., pp. 660-669.
"API Recommended Practice for Core-Analysis Procedure", Am. Petroleum Inst., Dalla First Edition, 8/60, pp. 2-55.
Reports: "Computed Tomographic Analysis of Meteorite Inclusions", Science, vol. 219, Jan. 28, 1983, pp. 383-384.

Primary Examiner—Carolyn E. Fields
Assistant Examiner—David P. Porta
Attorney, Agent, or Firm—Alexander J. McKillop; Michael G. Gilman; George W. Hager, Jr.

[57] ABSTRACT

A core sample of a porous media of identified porosity at atmospheric conditions is saturated with a fluid having an identified X-ray attenuation coefficient. The fluid saturated sample is scanned with X-rays. Confining stress is applied to the sample and the sample is again scanned with X-rays. Porosity of the sample at confining stress is then determined from the porosity at zero confining stress, the X-ray attenuation coefficient of the saturating fluid, and X-ray attenuation coefficients determined from the scanning of the sample at both atmospheric conditions and at confining stress. Pore volume compressibility is determined from the changes in porosity and X-ray attenuation coefficients from atmospheric to confining stress conditions.

6 Claims, 4 Drawing Sheets

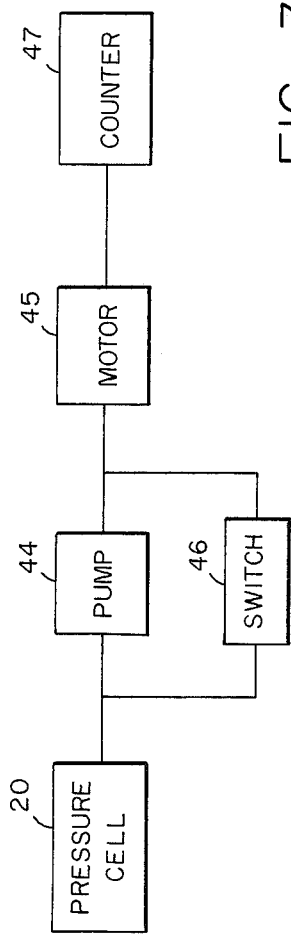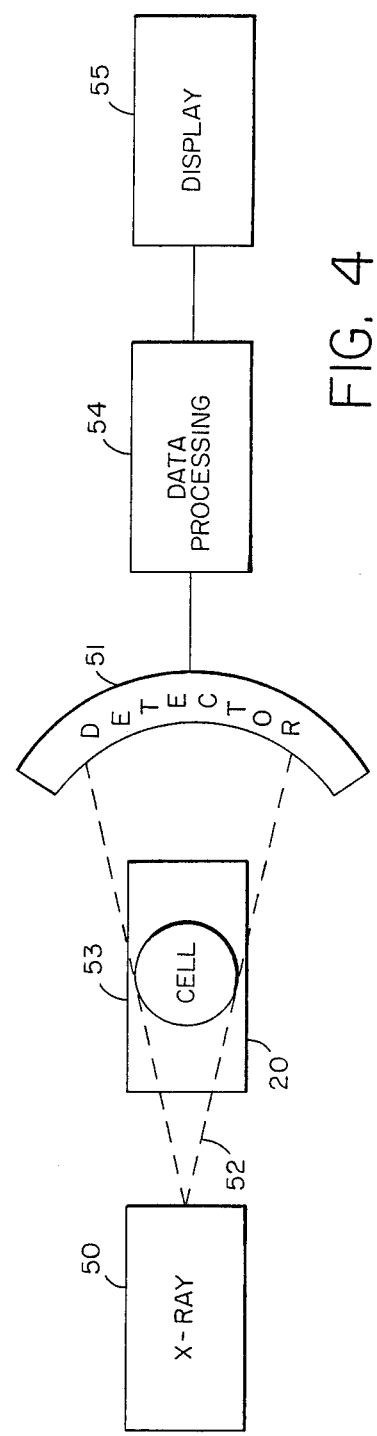

METHOD FOR DETERMINING PORE VOLUME COMPRESSIBILITY OF A POROUS MATERIAL

BACKGROUND OF THE INVENTION

In the production of minerals, e.g., oil and gas, certain lithological properties of a subterranean reservoir must be determined. Two of the most important of these properties are the porosity and pore compressibility of the reservoir. Porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. Normally, porosity is determined by taking core samples from the reservoir and carrying out well-defined measurement techniques on the samples. There are several techniques available for making such measurements, many of which are described in PETROLEUM PRODUCTION ENGINEERING—DEVELOPMENT by L. D. Uren, Fourth Edition, McGraw-Hill Book Company, Inc., 1956, pps. 660-669. Another standard reference is American Petroleum Institute, *API Recommended Practice for Core-Analysis Procedure*, API RP 40, 1960, 55 pp. Such porosity measurements are performed on the core samples at ambient pressure conditions. However, the effect of overburden pressure or confining stress on the porosity of a sample of a reservoir rock is an important factor in determining oil and gas reserves, as well as in estimating reservoir performance. Accurate determinations of pore volume compressibility are needed for correcting core sample porosity to reservoir stress conditions and for estimating the changes in reservoir pore volume due to pressure depletion. Such a pore volume compressibility determination has been routinely carried out by a fluid expulsion procedure known as "brine squeeze-out". In this procedure a cylindrically-shaped sample of known pore volume is saturated with brine and placed in a rubber-sleeved core holder. Confining stress is applied at selected values of sleeve pressure, and the brine is allowed to flow from one face of the sample into a pipette open to atmospheric pressure. The change in pore volume is considered to be the amount of brine expelled at any particular confining pressure. For consolidated rock samples the reference pressure, representing zero stress, is typically 200 to 450 psi. This is presumably the pressure at which the rubber sleeve fits snugly around the sample. Therefore, any brine expelled at higher pressures indicates actual pore volume change and not the volume of brine displaced from between the rock and the rubber sleeve. The pore volume at the "zero stress" condition is presumed to be the same as the pore volume measured at ambient conditions outside of the core holder.

Two types of reservoir rocks, accounting for a large fraction of reserves, create difficulties when interpreting data from the brine squeeze-out. Unconsolidated sands tend to compress significantly at very low stresses. In fact, the confining pressure required to seat the rubber sleeve can result in the loss of several percent of the ambient pore volume. The reference pressure chosen for tests with unconsolidated sand may not be the zero stress condition that is required. This condition would lead to the underestimation of porosity correction. The other type of sample which causes difficulty is characterized by vuggy porosity or very coarse grain size, i.e., rocks with large pores. At low pressures, the stiffness of the rubber sleeve presents the sleeve from invading the large surface pores. At increasing pressure, however, the sleeve invades these pores and brine is displaced which is not attributable to an actual reduction of pore volume. This would result in an apparent porosity loss which is much higher than the actual value.

Consequently, there is a crucial need for porosity and pore compressibility measurements under reservoir confining stress conditions so that accurate calculation of reserves and changes in reserves due to production depletion can be made. It is this need for core porosity and pore volume compressibility measurements at reservoir stress conditions that the present invention is directed.

SUMMARY OF THE INVENTION

In accordance with the present invention, the porosity and pore compressibility of a porous media is determined by the use of X-ray scanning in the presence of confining pressure. More particularly, the porosity of the core sample is determined at atmospheric reference pressure (i.e. zero confining stress). The sample is then saturated with a fluid of predetermined X-ray attenuation coefficient. The fluid saturated sample is placed in a confining pressure cell and scanned with X-rays at a plurality of points along the sample. A first set of computed tomographic images are produced at the plurality of points along the sample. From these images, an X-ray attenuation coefficient at zero confining stress is determined. The pressure is then increased within the cell to provide confining stress to the sample. The sample is then scanned with X-rays at a plurality of points along the sample. A second set of computed tomographic images are produced at said plurality of points along the sample for the confining stress. From these images, an X-ray attenuation at confining stress is determined. Porosity is then determined at confining stress from the determinations of sample porosity at zero confining stress, saturating fluid X-ray attenuation coefficient, sample X-ray attenuation coefficient at zero confining stress, and sample X-ray attenuation coefficient at confining stress.

In a further aspect, porosity of the sample is determined for a plurality of confining stress conditions. An interval is selected between a pair of such confining stresses. Both the change in confining stress and the change in porosity is determined over this select interval. Pore compressibility of the sample over the select interval is then determined from the changes in confining stress and porosity and the porosity of the sample at the initial confining stress for the select interval.

BRIEF DESCRIPTION OF THE DRAWINGS

FIG. 3 is a block diagram of the system for supplying confining pressure to the pressure cell of FIG. 2.

FIG. 4 is a pictorial view of a CT scanning system for use in scanning the sample of porous material in the confining pressure cell of FIG. 2 with X-rays in accordance with the method of the present invention.

DESCRIPTION OF THE PREFERRED EMBODIMENT

Figure 1:
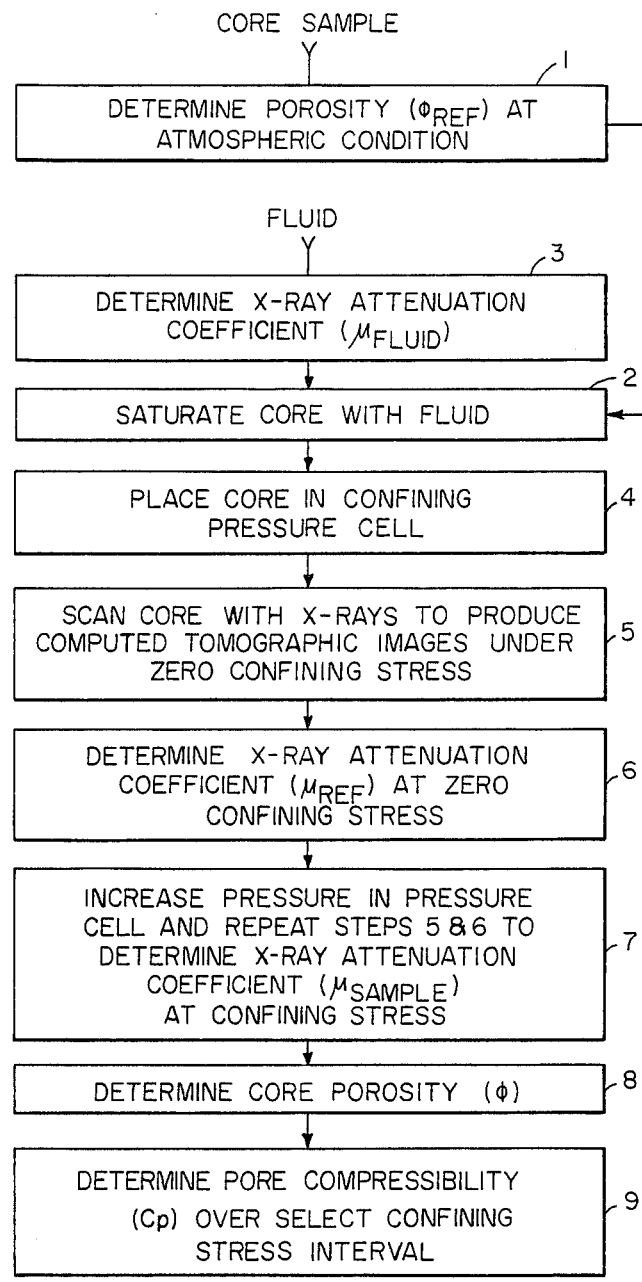
FIG. 1 is a flow chart depicting the steps in the method of the present invention for determining porosity and pore compressibility of a porous media.

The present invention is directed to a new and improved method for measuring reservoir porosity and pore compressibility with changes in reservoir stress conditions that does not depend on measuring the volume of fluid expelled from reservoir core samples. Such method employs the computed tomography (CT) technology. CT scanning instruments produce a cross-sectional view through a subject material along a chosen axis. The advantages of CT scanning over conventional radiography is found in its ability to display the electon density variations with the object scanned in a two-dimensional X-ray image. Such technology has been in use in the medical field for a number of years as described in U.S. Pat. No. 4,157,472 to Beck, Jr. and Barrett and U.S. Pat. No. 4,399,509 to Hounsfield.

Many other applications of CT scanning have also been made. For example, in an article entitled, "Computed Tomographic Analysis of Meteorite Inclusions", *Science*, pps. 383–384, Jan. 28, 1983, there is described the non-destructing testing of meteorites for isotropic anomalies in calcium- and aluminum-rich inclusions of hererogeneous materials, such as Allende. The CT scanning equipment described in such article is the Deltascan 2020 from Technicare. In a further application, CT scanning has been applied to the non-destructive testing of wood materials, such as for disease in living trees, see U.S. Pat. No. 4,283,629 to Habermehl. In a yet further application, CT scanning has been applied to the examination of non-living objects, such as motors, ingots, pipes, etc., see U.S. Pat. No. 4,422,177 to Mastronardi et al.

More recently, the CT scanning technology has been applied to the field of energy research for examining the interior of stationary or slowly changing earth materials, such as core samples taken from subterranean oil or gas reservoirs. One such application is described in U.S. Pat. No. 4,649,483 to Dixon, Jr. A multi-phase fluid saturation in a core sample of the porous media, such as from an oil or gas reservoir, is determined from X-ray scans of differing energies in both fluid saturated and fluid-extracted states. The extracted fluids are also scanned at differing X-ray energies. The computed tomographic images produced are utilized in the determination of the X-ray mass attenuation coefficients for the core sample and the extracted fluids. From these mass attenuation coefficients, the weight fractions and volume fractions of the extracted fluids are determined.

In U.S. Pat. No. 4,688,238 to Sprunt et al, CT scanning has been utilized for determining the range of confining stresses which can be applied to an elastic jacket surrounding a core sample of a porous media during a measurement of pore volume characteristics. The sample, with its surrounding jacket, is placed in a confining pressure cell where the pressure is varied over a plurality of points. The sample is X-ray scanned at each stress point and CT images produced. From these CT images a range of confining stresses is determined over which pore volume parameters can be measured without being affected by improper conformance of the jacket to the surface of the sample.

In another application of CT scanning to characterize a porous media, U.S. application Ser. No. 872,341, filed June 9, 1986 to Sprunt et al, identifies a method for identifying the porosity and drilling mud invasion of a core sample from a subsurface reservoir. More particularly, porosity of the core sample is determined from the ratio of measured pore volume to measured bulk volume. The core sample is scanned with X-rays and CT images produced. The concentration of drilling mud solid in the core sample is identified from the density effect of the drilling mud solid on the CT images. The porosity determination is corrected for the volumetric concentration of drilling mud solid in the pore spaces of the core sample.

The present invention employs such CT scanning technology to determine porosity and pore volume compressibility of a porous media, such as a core sample from a subterranean reservoir, placed under a confining stress as will hereinafter be described. Referring now to FIG. 1, there is shown a flow chart of the method utilized in the present invention to determine porosity and pore compressibility. The porosity of the core sample is firstly determined at atmospheric conditions in step 1 by any of several conventional techniques such as described in the aforementioned PETROLEUM PRODUCTION ENGINEERING DEVELOPMENT. The core sample is then fluid saturated in step 2 with a liquid or a gas, such as a brine or air for example, whose CT number, or X-ray attenuation coefficient, is known or can be measured in step 3 in accordance with the teaching of the aforementioned U.S. Pat. No. 4,399,509 to Hounsfield; U.S. Pat. No. 4,283,629 to Habermehl; and U.S. Pat. No. 4,649,483 to Dixon, Jr. The core sample is next placed in a confining pressure cell in step 4. Such a confining pressure cell is shown in FIG. 2.

Figure 2:
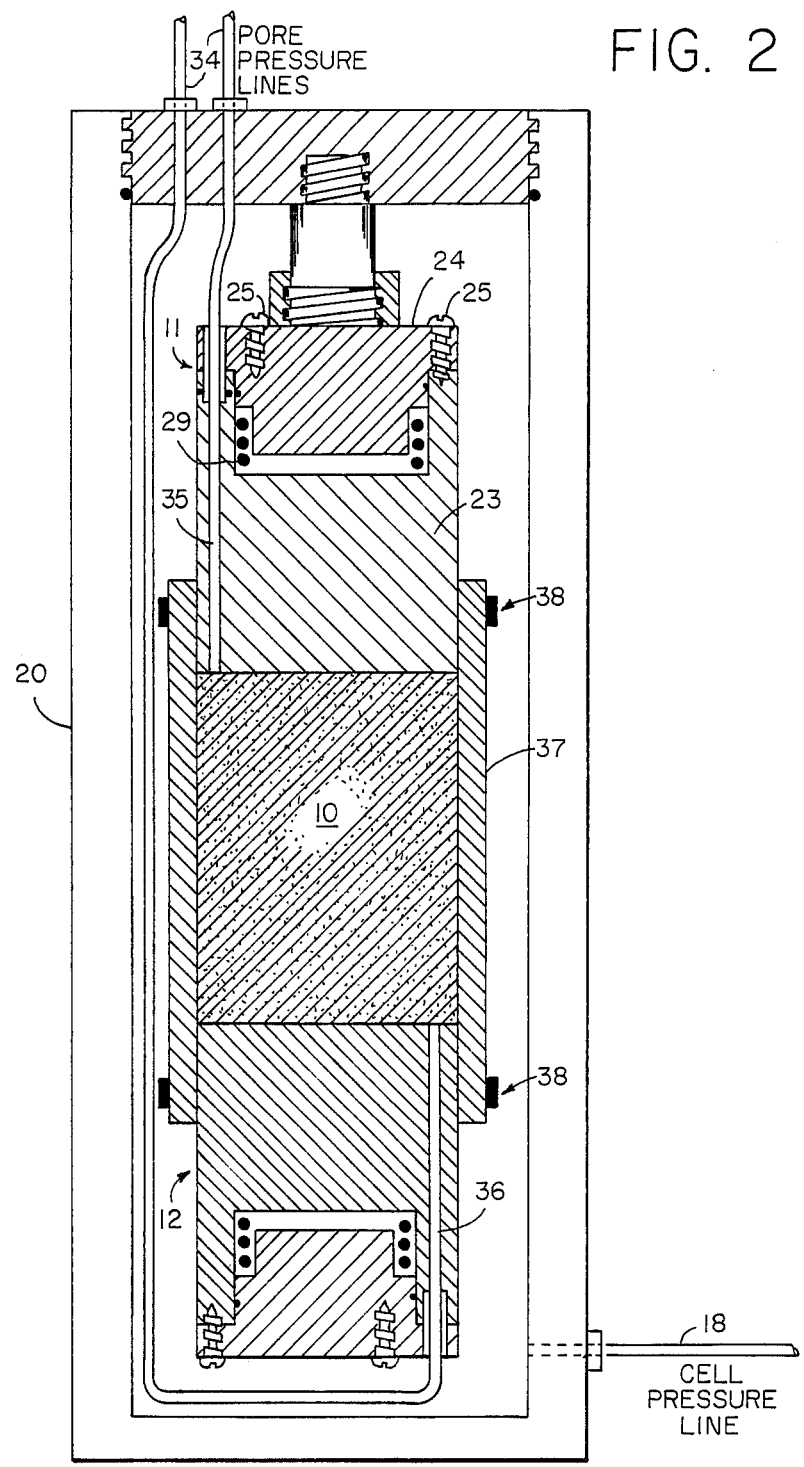
FIG. 2 is a cross-sectional view of a confining pressure cell housing a sample of porous material to be examined in accordance with the method of the present invention.

Referring now to FIG. 2, the core sample 10 is mounted between a housing 11 and a housing 12 and is enclosed within a confining pressure cell 20 for subjecting the core sample to varying stress conditions. The confining stress condition within the cell 20 is established by the cell pressure line 18.

Housing 11 comprises an annular member 23 and a cover member 24. Such cover member 24 encloses the open end of the annular member 23 and is secured by screws 25. The face of the member 23 is maintained in good contact with the core sample 10 through spring-loading provided by one or more spring-like members 29.

Pore pressure lines 34 provide the desired fluid pressure to the core sample 10 by way of the passageways 35 and 36 in the housings 11 and 12, respectively.

The core sample 10 and portions of housings 11 and 12 are surrounded by a jacket, or sleeve, 37, which may be made of an impermeable elastic material, such as rubber, for example. The jacket 37 is secured to the housings 11 and 12 and the core sample 10 by the clamps 38.

The confining stress applied to cell 20 through cell pressure line 18 is supplied by the system illustrated in FIG. 3. Line 18 is connected to pump means 44 which is operated by motor 45. Pump means 44 is of the type which allows accurate measurement of the amount of fluid pumped, e.g., a screw-feed, positive-displacement pump which has a capacity forward of its displacement piston sufficient to store the volume of non-compressible fluid necessary for use in the present invention. This negates the need for the separate fluid reservoir as is well understood by those skilled in the art, although such a reservoir could be easily provided. Motor 45 is preferably of the type commonly referred to as a stepping motor so that it moves pump means 44 in discrete increments to force non-compressible fluid through pressure supply line 18 into cell 20 to expand jacket 37 into contact with core sample 10. The stress within the cell 20 may be varied over a plurality of pressure points. A counter 47 records the number of steps of motor 45. Pressure-sensitive switch 46 is connected into pressure supply line 18 to shut off motor 45 when a preset pressure has been reached. By counting the number of steps of motor 45 and knowing the corresponding displacement of pump 44 for each step, the exact amount of fluid which is necessary to reach the preset pressure can be determined.

After installing the core sample in the pressure cell 20 of FIG. 2 and connecting the confining pressure line from the system of FIG. 3, the next step is the scanning of the core sample with X-rays as shown in step 5 of FIG. 1. A computed tomographic (CT) scanning system for carrying out such X-ray scanning is illustrated in FIG. 4.

Referring now to FIG. 4, X-ray energy provided by the X-ray tube 50 passes through the core sample 10 within the pressure cell 20 and falls on the detector array 51. Rotation of the pressure cell within the X-ray fan beam 52 is provided by the gantry 53. In an alternative embodiment, the core sample 10 may remain stationary and the gentry may be used to rotate the X-ray tube 50 and detector 51 about the core sample. In medical applications, CT scanning rates are usually in the order of 2 to 9 seconds. However, patient dose limitations are of no concern in the present application, and scan times of the core sample can be up to 1 minute per scan, or even longer, if desired. The output of the detector array 51 is passed through the data processing unit 54 to the display unit 55. After a desired number of scans are completed for a core sample slice, the sample is indexed one slice-width through the X-ray fan beam to place the next adjacent sample slice within the path of the X-ray fan beam. In this manner, a 3-D tomographic presentation is made on the display unit 55 of the entire sample by compositing the cross-sectional view of each of the scan slices. Such a CT scanning system, while not forming a part of the present invention, is used in accordance with the method of the present invention to determine the conformance of the jacket 37 to the surface of the core sample 10 under varying stress conditions.

For a more detailed description of CT scanning systems which may be utilized in the method of the present invention, reference may be made to each of the aforementioned U.S. patents and the referenced Science article, the teachings of which are incorporated herein by reference. A particularly suitable detector array 51 for use in the present invention for a 100 micron resolution would comprise a 1024×1 linear array of photodiodes on a 0.001 inch center-to-center spacing with pixel (picture element) aperture of 0.001 inch by 0.1 inch. An example of such an array is the Reticon 1024S/fiber optic faceplate. For a lower 250 micron resolution, a 200×1 linear array of photodiodes on a 0.01 inch center-to-center spacing with pixel apertures of 0.01 inch to 0.1 inch would be suitable. An example of such an array is that used in digital mammography equipment supplied by Bio-Imaging Research, Inc. Optically coupled to the input surfaces of the photodiode arrays are scintillation arrays comprised of a plurality of discrete scintillators having X-ray sensitive fluorescent materials individually and optically coupled to the input surfaces of the discrete photidiodes. Such materials may comprise $CdWO_4$, $C_5I$, $GdOBr$ or $LaOBr$, among others. Such combination of scintillators and photodiodes provides for a complete scintillation counter. The photodiodes provide electrical signals whose heights are proportional to the X-ray energy falling upon the surfaces of the scintillators. The fan beam of such X-ray energy is identified by the dashed lines 52 in FIG. 4 as falling upon the detector array 51 after having passed through the core sample 10. After suitable amplification, the signals are digitized for use in producing the desired tomographic display from which the X-ray attenuation coefficient for zero confining stress is determined in step 6 as will be more fully described hereinafter.

Sufficient confining stress is applied to the pressure cell 20 to press the elastic jacket 37 into contact with the surface of the core sample 10. The pressure is then varied through a plurality of points and the sample is scanned with X-rays at a plurality of locations for each of the pressure points as shown in step 7. For greatest accuracy, images should be taken in consecutive slices so that the entire volume of the sample is scanned. A computed tomographic image of the sample is produced for each of the X-ray scans. The resulting CT images are, in effect, two-dimensional maps of CT number ($N_{CT}$). Such CT number is a numerical measure of the X-ray absorption properties of the sample of material being scanned by the X-ray fan beam and is routinely provided by the CT scanning system, as is more fully described in the aforementioned U.S. Pat. Nos. 4,283,629 and 4,399,509. Such a CT number is defined as:

$$N_{CT} = (\mu M - \mu W)/\mu W \times 1000 \tag{1}$$

where $\mu$ = X-ray linear attenuation coefficient,
M = material (or fluid) scanned, and
W = fluid (such as water)

From these measured CT numbers and previously measured values for $\mu W$, the X-ray attenuation coefficients are determined. After repeating the X-ray scan of the core sample for a plurality of confining stresses the porosity at each confining stress is determined in step 8 in accordance with the following relationship:

$$\phi = [(\phi_{ref} - 1)/(\mu_{ref} - \mu_{fluid})/ \times (\mu_{sample} - \mu_{fluid})] + 1 \tag{2}$$

where $\phi$ = porosity at confining stress,
$\mu_{sample}$ = X-ray attenuation coefficient of the fluid saturated sample at the confining stress,
$\phi_{ref}$ = atmospheric reference porosity of the sample before fluid saturation,
$\mu_{ref}$ = X-ray attenuation coefficient of the sample at zero confining stress, and
$\mu_{fluid}$ = X-ray attenuation coefficient of the fluid in the sample.

Figure 5:
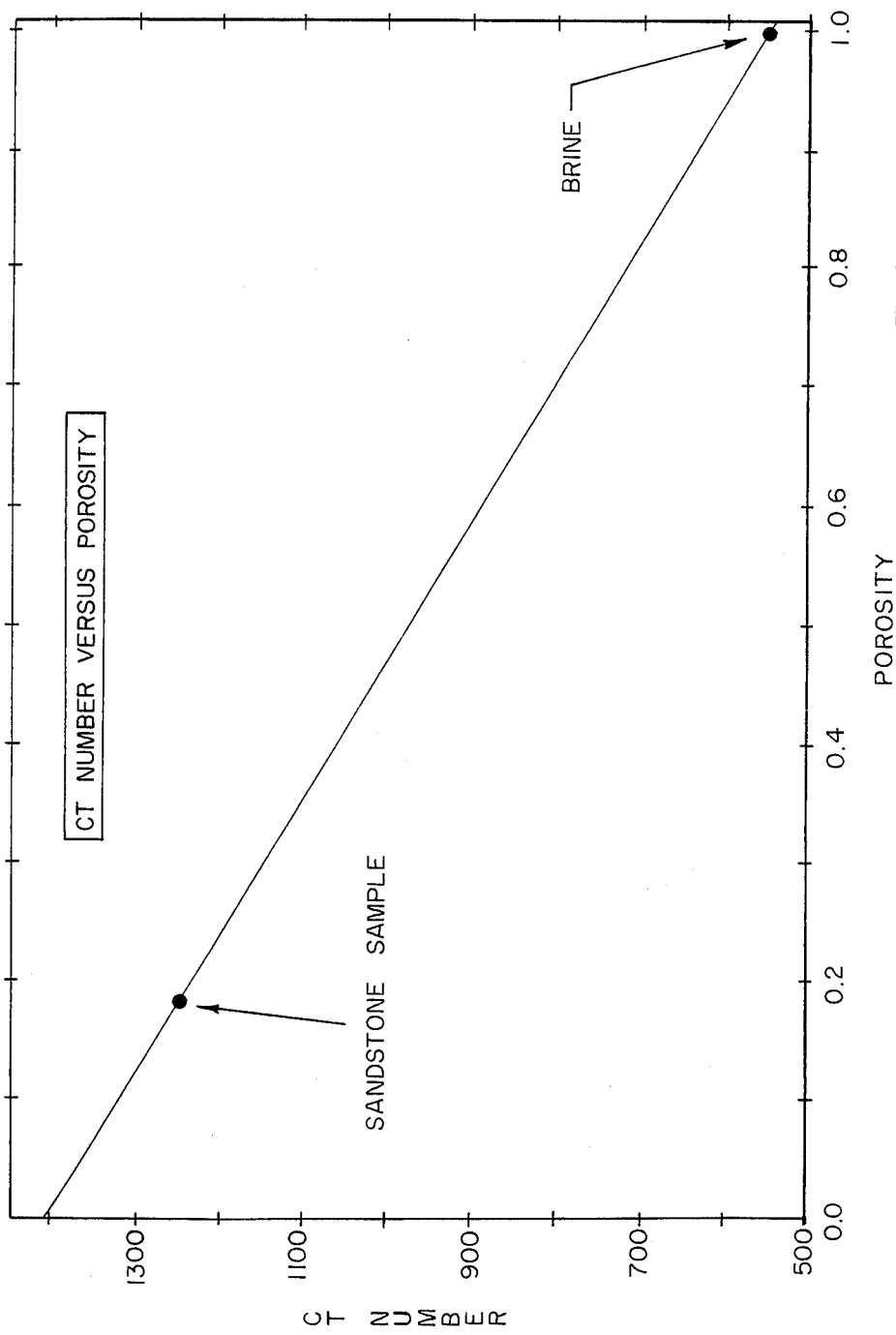
FIG. 5 is a plot of CT number versus porosity for a core sample housed in the confining pressure cell of FIG. 2 and scanned with X-rays from the CT scanning system of FIG. 4.

The X-ray linear attenuation coefficient $\mu$ of the fluid-filled sample is the linear combination (by volume) of the attenuation coefficients of the pore fluid and the solid components. This mixing law is shown in FIG. 5. If any two points along the mixing line can be determined, then the measurements of X-ray attenuation of a sample can be used to determine porosity as follows:

$$\mu_{sample} = (X_{fluid})(\mu_{fluid}) + (X_{solid})(\mu_{solid}) \tag{3}$$

where X=volume fraction of fluid or solid. Consequently, for changes in porosity, the average CT number is a linear function of porosity.

Having completed the porosity determinations, pore compressibility is determined in step 9 over a select interval of confining stress in accordance with the following relationship:

$$C_p = \Delta\phi/(\phi\Delta\delta) \qquad (4)$$

where:
  $C_p$ = pore compressibility,
  $\phi$ = porosity at initial confining stress of the select interval of confining stress,
  $\Delta\phi$ = change in porosity over the select interval of confining stress, and
  $\Delta\delta$ = change in confining stress over the select interval of confining stress, assuming no change in bulk volume.

In one example, a berea sandstone sample 1.5 inches in diameter is used to compare CT pore compressibility derived in accordance with the present invention with brine squeeze-out derived compressibility. Helium porosity of the sample is 18.6 percent. The pore volume is 10.4 cubic centimeters. The sample was saturated with 0.5 percent KCl brine and then subjected to one compression/decompression cycle with a maximum confining pressure of 5500 psi. It was then resaturated by flowing brine under 150 psi backpresure. During the second compression cycle, ten CT scans were performed at each confining pressure step. The time interval between each step was approximately one hour. At the end of the CT scanner experiment, the sample was removed from the pressure cell, dried, and resaturated with brine. Then, a sample of brine, placed inside an aluminum pressure cell, was CT scanned to obtain the 100 percent fluid reference point. The sample was loaded into another cell and subjected to brine squeeze-out, comprising the third compression cycle. Brine displacement was measured with a pipette at the same pressure steps used for the experiment performed on the scanner. Again, one hour intervals were used. For both the CT scanning and brine squeeze-out, confining stress was isotropic.

The X-ray images were stored on magnetic tape and analyzed on a Digital Equipment Corp. VAX computer. The average linear X-ray attenuation, expressed as CT number was determined for each image from identical regions of interest. These regions included all but the outer millimeter of the rock sample. Each scan was calibrated to water and aluminum standards. The X-ray tomographs represented sample slices one centimeter thick. The quantitative CT scan analyses are presented in Table 1.

TABLE 1
COMPRESSIBILITY EXPERIMENTS WITH
BEREA SANDSTONE

| Pressure (psi) | 400 | 1400 | 2400 | 3400 | 4400 | 5400 |
|---|---|---|---|---|---|---|
| CT Average | 1248.34 | 1250.09 | 1252.55 | 1254.00 | 1254.43 | 1255.00 |
| Brine Output (cc's) | 0.00 | 0.200 | 0.262 | 0.310 | 0.359 | 0.397 |
| CT Porosity | 0.1860 | 0.1840 | 0.1811 | 0.1794 | 0.1789 | 0.1782 |
| Squeeze-Out Porosity | 0.1860 | 0.1825 | 0.1814 | 0.1806 | 0.1797 | 0.1791 |

CT numbers are defined as:

$$CT = \frac{\mu - \mu_{water}}{\mu_{water}} 500 + 500 \qquad (5)$$

As can be noted, there is good correlation in the porosity determinations between the CT scanning method of the present invention for porosity and pore compressibility and the conventional brine squeeze-out method.

While a preferred embodiment of the method of the present invention has been described and illustrated, numerous modifications and alterations may be made without departing from the spirit and scope of the invention as set forth in the appended claims.

I claim:

1. A method for determining porosity in a porous media under confining stress, comprising the steps of:
  (a) determining the porosity of a sample of said porous media at atmospheric reference pressure,
  (b) saturating said sample with a fluid of predetermined X-ray attenuation.
  (c) placing the fluid saturated sample in a confining pressure cell,
  (d) scanning said fluid saturated sample with X-rays at a plurality of points along said sample at zero confining stress,
  (e) producing a first set of computed tomographic images at said plurality of points along said sample for zero confining stress,
  (f) determining from said first set of computed tomographic images an X-ray attenuation coefficient for zero confining stress,
  (g) increasing the pressure within said cell to provide a confining stress to said sample,
  (h) scanning said sample with X-rays at said plurality of points along said sample for said confining stress,
  (i) producing a second set of computed tomographic images at said plurality of points along said sample for said confining stress,
  (j) determining from said second set of computed tomographic images an X-ray attenuation coefficient for said confining stress, and
  (k) determining porosity of said sample at said confining stress from the determinations of sample porosity at atmospheric reference pressure, saturating fluid X-ray attenuation coefficient, sample X-ray attenuation coefficient at zero confining stress, and sample X-ray attenuation coefficient at said confining stress.

2. The method of claim 1 wherein said porosity at confining stress is determined in accoraance with the following relationship:

$$\phi = [(\phi_{ref}-1)/(\mu_{ref}-\mu_{fluid})/\times(\mu_{sample}-\mu_{fluid})]+1$$

where
  $\phi$ = porosity at confining stress,
  $\mu_{sample}$ = X-ray attenuation coefficient of the fluid filled sample at confining stress,
  $\phi_{ref}$ = atmospheric reference porosity of sample before fluid saturation,
  $\mu_{ref}$ = X-ray attenuation coefficient of the sample at zero confining stress, and
  $\mu_{fluid}$ = X-ray attenuation coefficient of the saturating fluid.

3. The method of claim 2 wherein said porosity is determined for a plurality of confining stresses.

4. The method of claim 3 further comprising the steps of:
(a) selecting an interval between a pair of confining stresses over which the pore compressibility of said sample is to be determined,
(b) determining the change in confining stress over the select interval,
(c) determining the change in porosity over said select interval, and
(d) determining the pore compressibility of said sample over said select interval from the determinations of confining stress change and porosity change and the porosity of said sample at the initial confining stress for said select interval.

5. The method of claim 4 wherein said step of determining pore compressibility is carried out in accordance with the following relationship:

$$C_p = \Delta\phi/(\phi\Delta\delta)$$

where:
$C_p$ = pore compressibility,
$\phi$ = porosity of said sample at the initial confining stress for said select interval,
$\Delta\phi$ = change in porosity over said select interval, and
$\Delta\delta$ = change in confining stress over said select interval.

6. The method of claim 1 wherein the X-ray attenuation coefficient of said saturating fluid is predetermined from computed tomographic images produced by X-ray scanning.

* * * * *